(12) United States Patent
Kunita

(10) Patent No.: US 8,323,200 B2
(45) Date of Patent: Dec. 4, 2012

(54) ULTRASOUND DIAGNOSTIC APPARATUS

(75) Inventor: Masanori Kunita, Mitaka (JP)

(73) Assignee: Hitachi Aloka Medical, Ltd., Mitaka-shi, Tokyo (JP)

( * ) Notice: Subject to any disclaimer, the term of this patent is extended or adjusted under 35 U.S.C. 154(b) by 475 days.

(21) Appl. No.: 12/477,266

(22) Filed: Jun. 3, 2009

(65) Prior Publication Data

US 2009/0299188 A1    Dec. 3, 2009

(30) Foreign Application Priority Data

Jun. 3, 2008   (JP) ................................. 2008-145605

(51) Int. Cl.
*A61B 8/14*    (2006.01)
*A61B 8/00*    (2006.01)
(52) U.S. Cl. ........................ 600/457; 600/453
(58) Field of Classification Search .................. 600/437, 600/453, 455, 457
See application file for complete search history.

(56) References Cited

U.S. PATENT DOCUMENTS

| | | | |
|---|---|---|---|
| 4,167,879 A | 9/1979 | Pedersen | |
| 4,176,351 A | 11/1979 | DeVita et al. | |
| 4,320,765 A | 3/1982 | Cathignol et al. | |
| 4,578,677 A | 3/1986 | Lewis | |
| 4,918,706 A | 4/1990 | Phillips et al. | |
| 5,022,400 A | 6/1991 | Walters | |
| 5,224,482 A | 7/1993 | Nikoonahad et al. | |
| 6,179,781 B1 | 1/2001 | Phillips | |
| 6,918,875 B2 | 7/2005 | Moriya et al. | |
| 6,953,434 B2 | 10/2005 | Hao et al. | |
| 6,960,169 B2 | 11/2005 | Mao et al. | |
| 7,094,204 B2 | 8/2006 | Banjanin et al. | |
| 7,338,450 B2 | 3/2008 | Kristoffersen et al. | |
| 7,698,948 B2 | 4/2010 | Asafusa et al. | |
| 7,887,487 B2 | 2/2011 | Hao et al. | |
| 2007/0282203 A1 | 12/2007 | Baba et al. | |
| 2008/0269612 A1 | 10/2008 | Kunita | |

(Continued)

FOREIGN PATENT DOCUMENTS

CN    86203861 U    11/1987

(Continued)

OTHER PUBLICATIONS

Chinese Office Action dated Mar. 23, 2011, issued in corresponding Chinese Patent Application No. 2009-10143784.2.

(Continued)

*Primary Examiner* — Michael Rozanski
(74) *Attorney, Agent, or Firm* — Westerman, Hattori, Daniels & Adrian, LLP

(57) ABSTRACT

A PSK modulator 20 applies digital modulation processing to an RF wave supplied from an RF wave oscillator 22, by means of phase shift keying (PSK) based on a periodical signal sequence supplied from a pattern generator 24, to thereby generate a continuous wave. The continuous wave output from the PSK modulator 20 is delayed in delay circuits 26I and 26Q and is then supplied, as a reference signal, to each of mixers of a receiving mixer 30. Each of the delay circuits 26I and 26Q delays the continuous wave by a delay amount in accordance with a depth of a target position and outputs a delayed reference signal. Thus, demodulation processing is performed with a correlation between a reception signal from the target position and the reference signal being enhanced, and Doppler information from the target position is selectively extracted by a Doppler information analyzing unit 44.

15 Claims, 12 Drawing Sheets

U.S. PATENT DOCUMENTS

2009/0312636 A1* 12/2009 Kunita .................... 600/437

FOREIGN PATENT DOCUMENTS

| EP | 1695665 A2 | 8/2006 |
| --- | --- | --- |
| EP | 1 769 747 A1 | 4/2007 |
| EP | 1 986 020 A2 | 10/2008 |
| JP | 2005-253949 A | 9/2005 |
| JP | 2006-014916 A | 1/2006 |
| JP | 2006288974 A | 10/2006 |
| JP | 2007330541 A | 12/2007 |
| WO | 2006/043603 A1 | 4/2006 |

OTHER PUBLICATIONS

Chinese Office Action dated Mar. 24, 2011, issued in related Chinese Patent Application No. 2009-10147985.X.
European Search Report dated Aug. 14, 2009, issued in corresponding European Patent Application No. 09006912.1.
European Search Report dated Jan. 28, 2011, issued in related European Patent Application No. 08007852.0.
Wilhjelm J E et al., "Coherent FM Doppler System", 1989 Ultrasonics Symposium Proceedings, Oct. 3, 1989, pp. 903-906.
European Search Report dated Oct. 5, 2009, issued in related European Patent Application No. 09007364.4.
Chinese Office Action dated Feb. 5, 2010, issued in related Chinese Patent Application No. 200810091287.8.
Masanori Kunita; "Range Measurement in Ultrasound FMCW System," Electronics and Communications in Japan, Part 3; vol. 90; No. 1; 2007; pp. 9-19.
USPTO Office Action dated Jan. 28, 2011, issued in U.S. Appl. No. 12/107,461.
USPTO Office Action dated Jun. 22, 2011, issued in U.S. Appl. No. 12/107,461.
USPTO Office Action dated Sep. 15, 2011, issued in U.S. Appl. No. 12/480,874.
Notice of Allowance and Fees Due dated Oct. 11, 2011, issued in related U.S. Appl. No. 12/107,461.
Notice of Allowance and Fees due dated Apr. 24, 2012, issued in copending related U.S. Appl. No. 12/477,266.
Final Office Action dated Mar. 15, 2012, issued in related U.S. Appl. No. 12/480,874.
Michael Ellis, "Using Mixers in Radio Communications", Mar. 21, 2004, retrieved from the Internet: URL:http://web.archive.org/web/20040321152312/http://michaelgellis.tripod.com/mixerscom.html, (9 pages), cited in European Office Action dated Jun. 13, 2012.
European Office Action dated Jun. 13, 2012, issued in corresponding European application No. 09006912.1.
Notice of Allowance and Fees Due dated Sep. 5, 2012, issued in related U.S. Appl. No. 12/480,874.

* cited by examiner

FIG. 5

ULTRASOUND DIAGNOSTIC APPARATUS

BACKGROUND

1. Technical Field

The present invention relates to an ultrasound diagnostic apparatus, and more particularly to an ultrasound diagnostic apparatus in which a modulated continuous wave is utilized.

2. Related Art

Continuous wave Doppler is a known ultrasound diagnostic apparatus technology in which a continuous wave is employed. In continuous wave Doppler technology, a transmission wave formed as a sinusoidal wave of several MHz is continuously radiated into a living organism, and a reflection wave from within the living organism is then continuously received. The reflection wave includes Doppler shift information generated by a moving element (e.g. blood flow) within the living organism. Accordingly, by extracting the Doppler shift information and applying frequency analysis thereto, a Doppler waveform which reflects information of velocity of the moving element, for example, can be formed.

Continuous wave Doppler technology in which a continuous wave is utilized is generally superior to Pulse Doppler, in which a pulse wave is utilized, for rapid acquisition of velocity measurements. Under such circumstances, the inventors of the present application have conducted research concerning continuous wave Doppler technology. In one of their achievements, the present inventors proposed the technology concerning Frequency Modulated Continuous Wave Doppler (FMCW Doppler) disclosed in JP 2005-253949 A.

However, use of a continuous wave makes continuous wave Doppler technology less suited for measuring a position. As such, typical continuous wave Doppler devices (i.e., devices in which the FMCW Doppler is not utilized) were unable to perform position measurement. In this regard, the present inventors proposed, in JP 2006-14916 A, a technology which enabled measurement of a position of a tissue within a living organism, in addition to measurement of the velocity of a tissue within the living organism, by using FMCW Doppler.

The FMCW Doppler technology described in the above-noted publications is a revolutionary technology providing a potential for new forms of ultrasound diagnosis. The present inventors have continued to research and improve this landmark technology.

SUMMARY

The present invention was made in view of the above circumstances, and advantageously provides an improved technology for extracting Doppler information from a target position by using a continuous wave.

In order to achieve the above advantages, in accordance with an aspect of the invention, there is provided an ultrasound diagnostic apparatus including a transmission signal processing unit that outputs a transmission signal which is a continuous wave having been digitally modulated based on a periodical signal sequence; a transmitting/receiving unit that transmits a transmission wave corresponding to the transmission signal to a living organism and receives a reception wave associated with the transmission wave from the living organism, to thereby obtain a reception signal; a reception signal processing unit that applies demodulation processing to the reception signal by using a reference signal formed based on the transmission signal, to thereby obtain a demodulated signal; and a Doppler information extraction unit that extracts Doppler information from the demodulated signal, wherein Doppler information from a target position within the living organism is selectively extracted.

In the above aspect, by adjusting a correlation between a periodical signal sequence of a reception signal obtained from a target position within a living organism and a periodical signal sequence of a reference signal, for example, a reception signal from the target position can be extracted as a signal component having a relatively high degree of correlation with the reference signal. In addition, by extracting Doppler information from the reception signal by using a bandpass filter or a low pass filter, for example, selective extraction of the Doppler information from the target position can be achieved. Here, in the above aspect, phase-shift keying, frequency shift keying, amplification shift keying, or the like can be utilized as digital modulation processing. Further, it is desirable that the waveform of the reference signal and the waveform of the transmission signal are completely identical. However, the reference signal and the transmission signal may be in a correspondence relationship, in which their waveforms can be considered to be substantially identical.

According to the present invention, extraction of Doppler information from a target position can be achieved by using continuous waves which have been subjected to digital modulation.

BRIEF DESCRIPTION OF THE DRAWINGS

A preferred embodiment of the present invention will be described in detail by reference to the following figures, wherein:

FIG. 5 is a view for explaining the relationship between a voltage output from the multiplier and the phase of a reference signal;

DETAILED DESCRIPTION

A preferred embodiment of the present invention will be described in detail with reference to the accompanying drawings.

Figure 1:
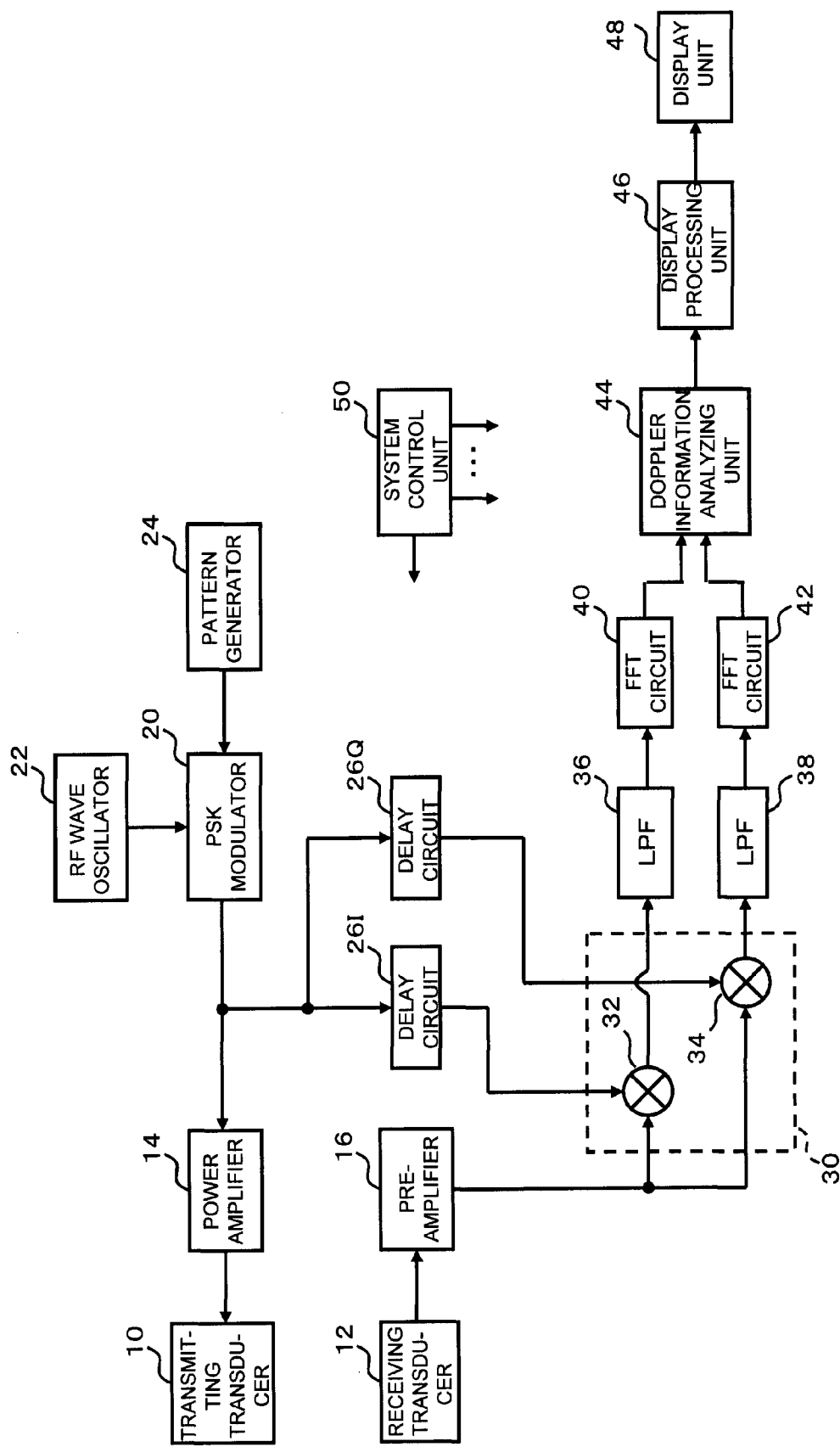
FIG. 1 is a functional block diagram illustrating the overall structure of an ultrasound diagnostic apparatus according to the present invention.

FIG. 1 is a functional block diagram illustrating the overall structure of an ultrasound diagnostic apparatus according to a preferred embodiment of the present invention. A transmitting transducer 10 continuously transmits a transmission wave into a living organism, and a receiving transducer 12 continuously receives a reflection wave from within the living organism. Thus, transmission and reception is performed by different transducers, and transmission/reception by means of a so-called continuous wave Doppler method technology is thus executed. The continuous waves utilized in the present embodiment are digitally modulated continuous waves which are formed by a PSK modulator 20.

The PSK modulator 20, by means of phase shift keying (PSK) based on a periodical signal sequence supplied from a pattern generator 24, applies digital modulation processing to an RF wave supplied from an RF wave oscillator 22, to thereby generate a continuous wave. The waveform of the continuous wave which is formed by phase shift keying (PSK) will be described with reference to explanation of the technological principle described below. The PSK modulator 20 outputs to a power amplifier 14 a continuous wave which has been digitally modulated.

The power amplifier 14 power-amplifies the digitally modulated continuous wave and then supplies the power-amplified digitally modulated continuous wave to the transmitting transducer 10. The transmitting transducer 10 transmits a transmission wave corresponding to the digitally modulated continuous wave. Then, a reflection wave from within the living organism is continuously received by the receiving transducer 12.

A preamplifier 16 applies reception processing such as low-noise amplification to a reception wave signal supplied from the receiving transducer 12 to thereby generate a receiving RF signal, which is output to a receiving mixer 30. The receiving mixer 30, which is a circuit for applying orthogonal detection to the receiving RF signal to generate a complex baseband signal, is composed of two mixers 32 and 34. Each of the mixers is a circuit which mixes the receiving RF signal with a predetermined reference signal.

The reference signal supplied to each mixer of the receiving mixer 30 is generated based on the digitally modulated continuous wave (i.e., the transmission signal). Specifically, the continuous wave output from the PSK modulator 20 is delayed in delay circuits 26I and 26Q, respectively. The continuous wave which is delayed by the delay circuit 26I is supplied to the mixer 32, and the continuous wave which is delayed by the delay circuit 26Q is supplied to the mixer 34.

The delay circuits 26I and 26Q delay the continuous wave by respective delay amounts in accordance with the depth of a target position, and thus output delayed reference signals. Each of the delay circuits 26I and 26Q can be formed of an n-stage shift register, for example. In this case, a tap for a delay amount corresponding to the depth of the target position is selected from n-stage taps of the shift register, and a reference signal in accordance with the depth of the target position (i.e. a delayed continuous wave) is output.

Here, the delay circuits 26I and 26Q perform delay processing by shifting the phases of the respective continuous waves by $\pi/2$ with respect to each other. Consequently, the mixer 32 outputs an in-phase signal component (I signal component) and the mixer 34 outputs a quadrature signal component (Q signal component). Then, high-frequency components of the in-phase signal component and the quadrature signal component are removed by LPFs (low pass filters) 36 and 38, respectively, which are provided downstream of the receiving mixer 30, so that demodulated signals having only a necessary bandwidth after detection can be extracted.

As will be described in detail in the following explanation of the technological principle of the present invention, a receiving mixer output signal (i.e. a demodulated signal), which is a result of mixing the receiving RF signal with the reference signal performed in each mixer, contains a large amount of reception signal components from the target position. The LPFs 36 and 38 extract a direct-current signal component contained in each of the reception signal components from the target position.

FFT circuits (fast Fourier transform circuits) 40 and 42 execute an FFT operation with respect to each of the demodulated signals (the in-phase signal component and the quadrature signal component). Consequently, the demodulated signals are transformed into a frequency spectrum in the FFT circuits 40 and 42. Here, the frequency spectrum output from the FFT circuits 40 and 42 is supplied in the form of frequency spectrum data with the frequency resolution $\delta f$, which depends on the circuit setting condition or the like.

A Doppler information analyzing unit 44 extracts Doppler information from the demodulated signals which are transformed into the frequency spectrum. At this time, as the delay relationship between the reference signal and the reception signal has already been adjusted in accordance with the depth of a target position within the living organism by the delay circuits 26I and 26Q, Doppler information from the target position can be selectively extracted. The relevance between the delay adjustment and the extraction of Doppler information from the target position will be described in detail with reference to explanation of the principle of the present invention. The Doppler information analyzing unit 44 extracts the Doppler information for each depth (each position) within the living organism, to thereby compute the velocity of a tissue within the living organism for each depth along the ultrasound beam (sound ray), and outputs the results in real time. Here, the velocity of a tissue at each position within the living organism may be computed in a two- or three-dimensional manner by scanning the ultrasound beam.

Based on the velocity of the tissue within the living organism for each depth (position), a display processing unit 46 creates a Doppler waveform or a graph including information concerning the depth velocity, for example, and causes a display unit 48 to display the Doppler waveform and the thus-created graphs in real time. Here, each of the units in the ultrasound diagnostic apparatus as shown in FIG. 1 is controlled by a system control unit 50. Specifically, the system control unit 50 performs transmission control, reception control, display control, and so on.

As described in general terms above, according to the present embodiment, an ultrasound wave corresponding to a continuous wave which has been subjected to digital modulation is transmitted and received to obtain a reception signal, and the delay relationship between the reference signal and the reception signal is adjusted in accordance with the depth of a target position within the living organism, and then demodulation processing is performed with the degree of correlation between the reception signal from the target position and the reference signal being thus increased, so that the Doppler information can be selectively extracted from the target position. Here, the principle for selectively extracting the Doppler information from a target position will be described in detail.

Figure 2:
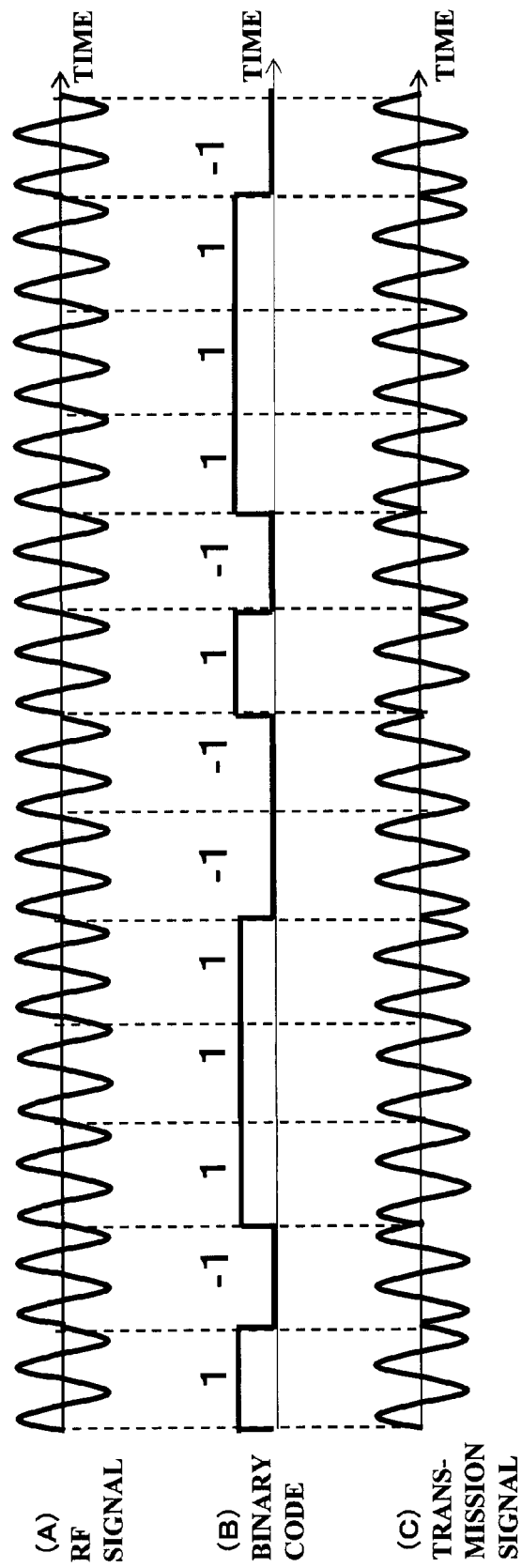
FIG. 2 is a view for explaining a transmission signal which is a continuous wave formed by PSK.

FIG. 2 explains a transmission signal which is a continuous wave formed by means of phase shift keying (PSK). FIG. 2(A) illustrates a waveform of an RF signal (RF wave) output from the RF wave oscillator (designated by reference numeral 22 in FIG. 1). An RF signal is a continuous wave having a fixed frequency (e.g. approximately 5 MHz). FIG. 2(B) illustrates an example of a periodical signal sequence output from the pattern generator (designated by reference numeral 24 in FIG. 1). The pattern generator generates a binary code whose value varies at random (a pseudo random signal), as illustrated in FIG. 2(B), for example.

FIG. 2(C) illustrates a modulated continuous wave (transmission signal) which is formed by the PSK modulator designated by reference numeral 20 in FIG. 1. The PSK modulator applies modulation processing by means of phase shift keying (PSK) to the RF signal illustrated in FIG. 2(A), based on the binary code illustrated in FIG. 2(B). Specifically, the PSK modulator maintains the phase of the RF signal during a bit period in which the binary code is "1" and inverts the phase of the RF signal (i.e. shifts the phase by 180 degrees) during a bit period in which the binary code is "−1", to thereby form a transmission signal shown in FIG. 2(C). As such, an ultrasound wave which is a continuous wave corresponding to the transmission signal shown in FIG. 2(C), for example, is output from the transmitting transducer (designated by reference numeral 10 in FIG. 1), and a reception signal from the living organism can be obtained via the receiving transducer (designated by reference numeral 12 in FIG. 1).

Figure 3:
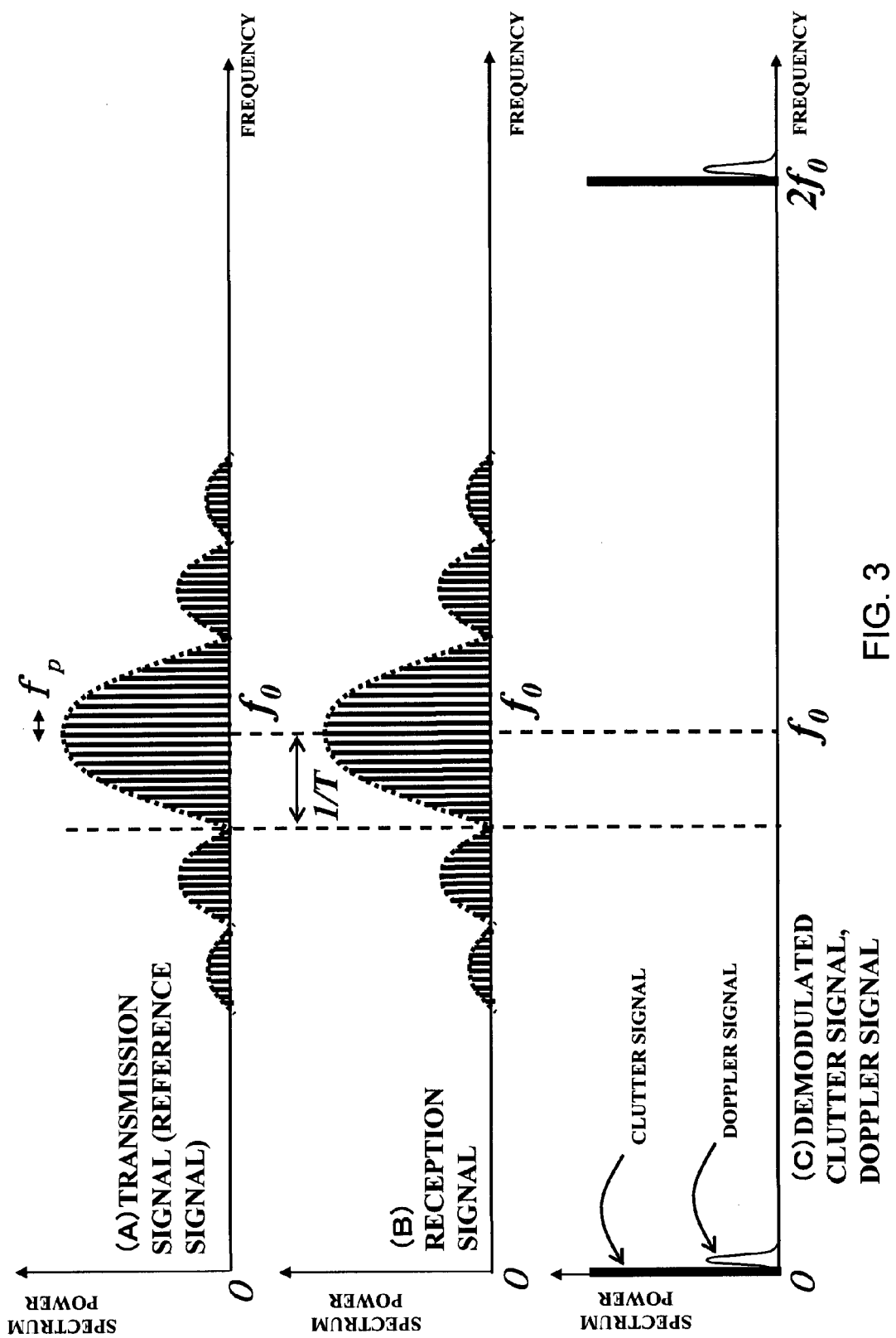
FIG. 3 is a view illustrating the frequency spectra of a transmission signal, a reception signal, and a demodulated signal.

FIG. 3 illustrates frequency spectra of a transmission signal, a reception signal, and a demodulation signal. Specifically, FIG. 3(A) illustrates the frequency spectrum of the transmission signal which is formed in the PSK modulator; i.e., a continuous wave which has been PSK modulated. The frequency $f_0$ is a frequency of the RF signal. The frequency interval of a sideband spectrum, with the frequency $f_0$ of the RF signal being a center, is a repetition frequency $f_p$ of the pseudo random signal (i.e. the binary code illustrated in FIG. 2(B)). Further, there exists a so-called null point where the power of the sideband spectrum around the frequency $f_0$ of the RF signal is 0 (zero). The frequency interval from the frequency $f_0$ to the null point is a reciprocal of the time interval T for 1 bit of the pseudo random signal (i.e., the binary code illustrated in FIG. 2(B)).

FIG. 3(B) illustrates the frequency spectrum of the reception signal. The reception signal has the same waveform as that of the transmission signal, if attenuation within the living organism is disregarded. Therefore, the frequency spectrum of the reception signal illustrated in FIG. 3(B) is substantially identical with the frequency spectrum of the transmission signal illustrated in FIG. 3(A). However, the phases are different between the transmission signal and the reception signal, in accordance with the propagation time of ultrasound within the living organism.

According to the present embodiment, delay processing is applied to the transmission signal which is formed by the PSK modulator (designated by reference numeral 20 in FIG. 1) to form the reference signal, and the reference signal is then used in the receiving mixer (designated by reference numeral 30 in FIG. 1) to thereby perform mixer processing with respect to the reception signal (i.e. multiplication of the reference signal and the reception signal). As will be described in detail below, in this mixer processing, the correlation between the reception signal from a depth corresponding to the phase of the reference signal having been subjected to delay processing (i.e. from a depth of the target position) and the reference signal is increased to the maximum, whereas the correction between the reception signal from depths other than the depth of the target position and the reference signal is drastically reduced.

FIG. 3(C) illustrates the frequency spectrum of the demodulated signal obtained by the mixer processing. The demodulated signal illustrated in FIG. 3(C) corresponds to a multiplication result between the reference signal and the reception signal in the case of maximum correlation. More specifically, the multiplication result between the reception signal from the target position and the reference signal having the phase matched to the depth of the target position is the demodulated signal illustrated in FIG. 3(C).

The demodulated signal illustrated in FIG. 3(C) contains a direct current signal component and a harmonic component which is of twice the frequency $f_0$ of the RF signal. The Doppler signal appears as attached to these components. Here, because the LPFs (designated by reference numerals 36 and 38 in FIG. 1) remove the harmonic component so that only the direct current signal components are extracted. Only the frequency spectrum of the direct current signal component illustrated in FIG. 3(C), is sent to the FFT circuits (designated by reference numerals 40 and 42 in FIG. 1). Then, in the Doppler information analyzing unit (designated by reference numeral 44 in FIG. 1), a Doppler signal is extracted from the frequency spectrum of the direct current signal component illustrated in FIG. 3(C), and the flow rate of blood existing at the target position, for example, is calculated based on the Doppler shift amount and so on. As orthogonal detection is performed in the receiving mixer (designated by reference numeral 30 in FIG. 1), the polarity of flow rate can also be determined. Also, the position of a blood vessel wall, for example, existing at the target position may be obtained by extracting a clutter signal from the frequency spectrum of the direct current signal component.

Here, the attenuation characteristics at the time of propagation of ultrasound within the living organism are called frequency dependent attenuation (FDA), and are known to be substantially in proportion to the frequency and the propagation distance in a soft tissue within the living organism. The FDA affects the shape of the frequency spectrum of the demodulated signal. More specifically, when compared to the frequency spectrum of a demodulated signal obtained from near the body surface, the frequency spectrum of a demodulated signal obtained from a deeper position suffers from greater attenuation. Accordingly, compensation processing for the frequency dependent attenuation within the living organism may be applied to the frequency spectrum output from the FFT circuits (designated by reference numerals 40 and 42). For example, a signal obtained from a deeper position is amplified to a greater degree, thereby cancelling a variation in the attenuation amount in accordance with the position (depth). It is also possible to apply compensation processing for the frequency dependent attenuation to the output from the receiving mixer (designated by reference numeral 30 in FIG. 1).

Figure 4:
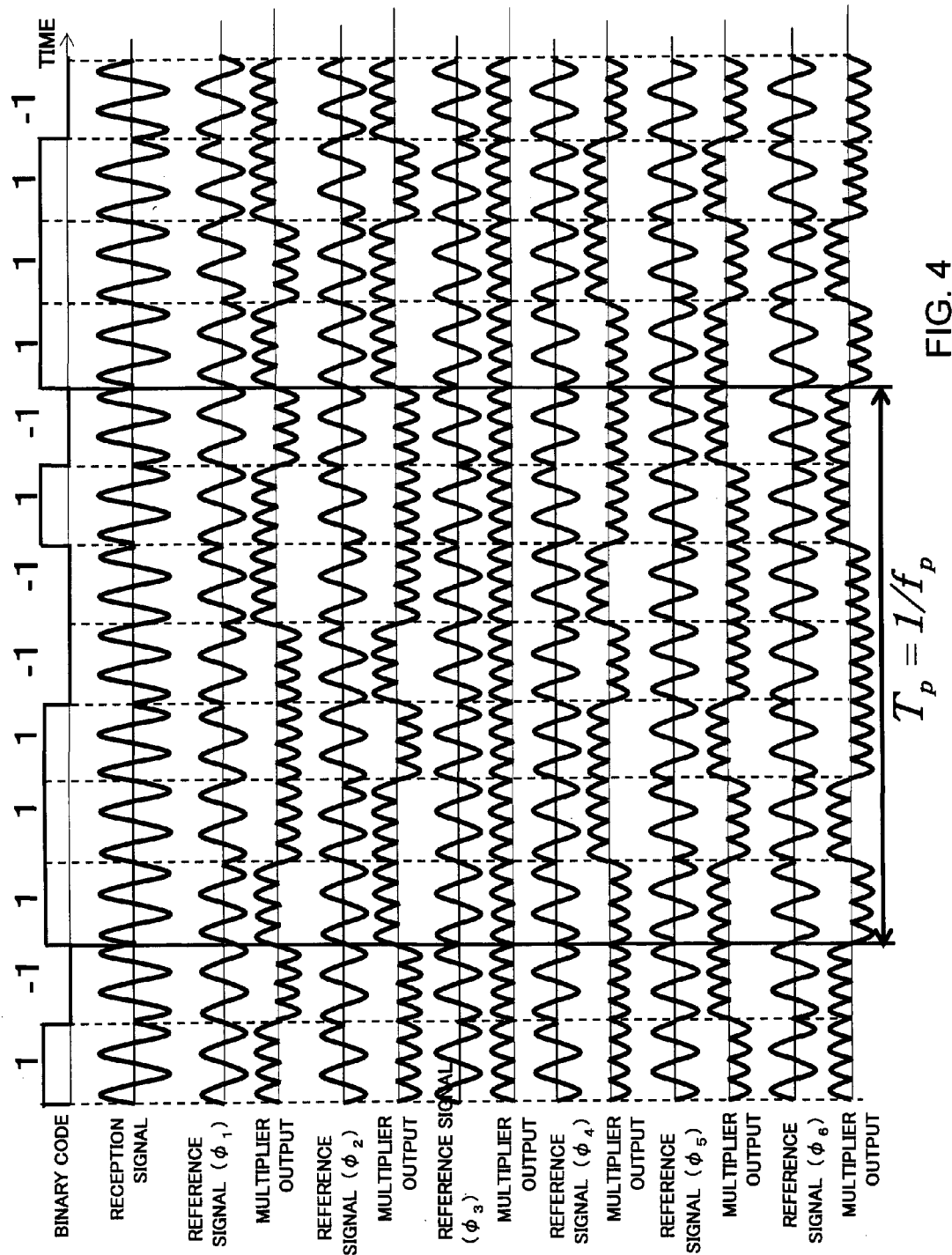
FIG. 4 is a view for explaining position selectivity according to the present embodiment.

FIG. 4 is a view for explaining the position selectivity according to the present embodiment. Sharpness of the correlation between a reception signal and a reference signal depends on a periodical signal sequence formed by the pattern generator (designated by reference numeral 24 in FIG. 1). In order to sharpen the correlation, it is advantageous to use a code sequence which is put into practical use by means of pulse compression or the like, such as a PN (Pseudo Noise) sequence, M sequence, or Gorey sequence, as a code sequence of a pseudo random signal which is a periodical signal sequence. Position selectivity when a PN code of n=3 is used, as a simple example, will be described with reference to FIG. 4.

The length of a PN code in the case of n=3 is $7(=2^3-1)$ bits. Because this sequence is repeated endlessly, this pseudo random pattern has a line spectrum of a reciprocal of the repetition period. If this signal is used to apply PSK modulation to a carrier wave having a frequency of $f_0$ with 2 phases, 0–π, the time waveform thereof is as illustrated in FIG. 2(C) described above.

The reception signal is a signal which is obtained by delaying the transmission signal by a delay time in accordance with the depth of a target and which is attenuated by a tissue. If such attenuation is disregarded, the waveform of the reception signal as illustrated in FIG. 4, for example, is obtained. Here, FIG. 4 illustrates results of multiplication (i.e. outputs of the multiplier) of the reception signal and the reference signal which is obtained by applying delay processing to the transmission signal, while varying the phase of the reference signal from $\phi_1$ to $\phi_6$.

As can be seen from FIG. 4, in the case of $\phi_3$, where the phases of the reference signal and the reception signal are identical with each other, the direct current component of the multiplier output (i.e. the mixer output) is maximized. Further, another feature obtained in the case where the phases of the reference signal and the reception signal correspond to each other is that only a carrier wave and a harmonic component thereof are alternating current components. The frequency spectrum of this signal is as illustrated in FIG. 3(C). As can also be seen from FIG. 4, when the phase is other than $\phi_3$, because a positive voltage and a negative voltage are generated at random as the multiplier outputs, the average voltage thereof is very small.

Figure 5:
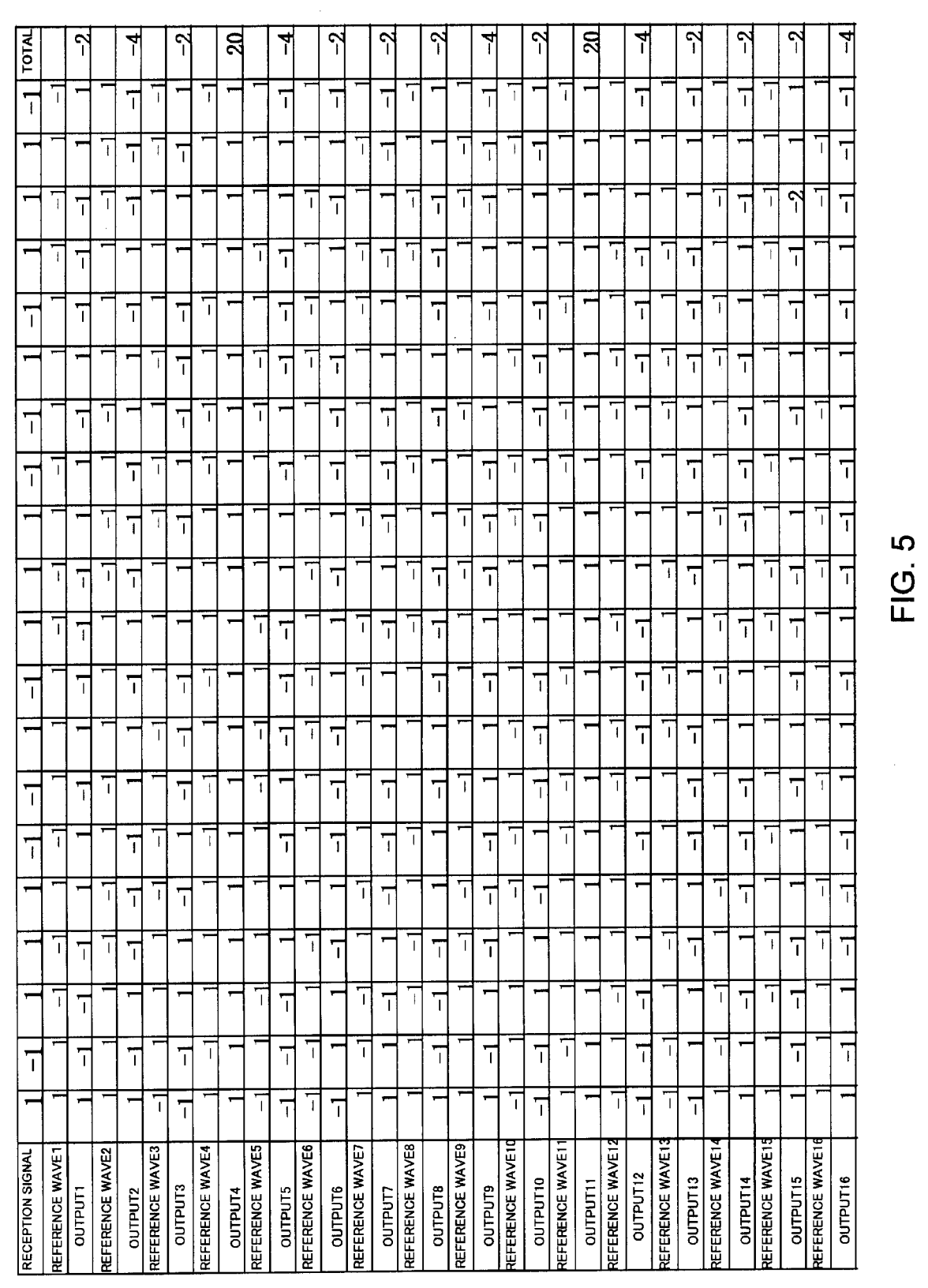

FIG. 5 is a chart for explaining the relationship between the voltage of a multiplier output and the phase of the reference signal. Specifically, FIG. 5 shows a PN pattern of the reception signal, a PN pattern of each of a plurality of reference signals having different phases (reference signal 1 to reference signal 16), results of multiplication of each reference signal and the reception signal (output 1 to output 16), and a sum of the multiplication results.

In FIG. 5, the sum value peaks for every repetition period of the PN pattern, and the voltages (the sum value) are extremely small at phases other than the peak phases. In this example, the length of the PN pattern is 7 bits, and the value in the right-end column indicates a summation result for about 3 periods. In other words, "20," which a sum of 20 bits, is the maximum value. Meanwhile, at phases other than the peak phase, the sum value is -2 or -4, which is extremely small as compared with "20."

Figure 6:
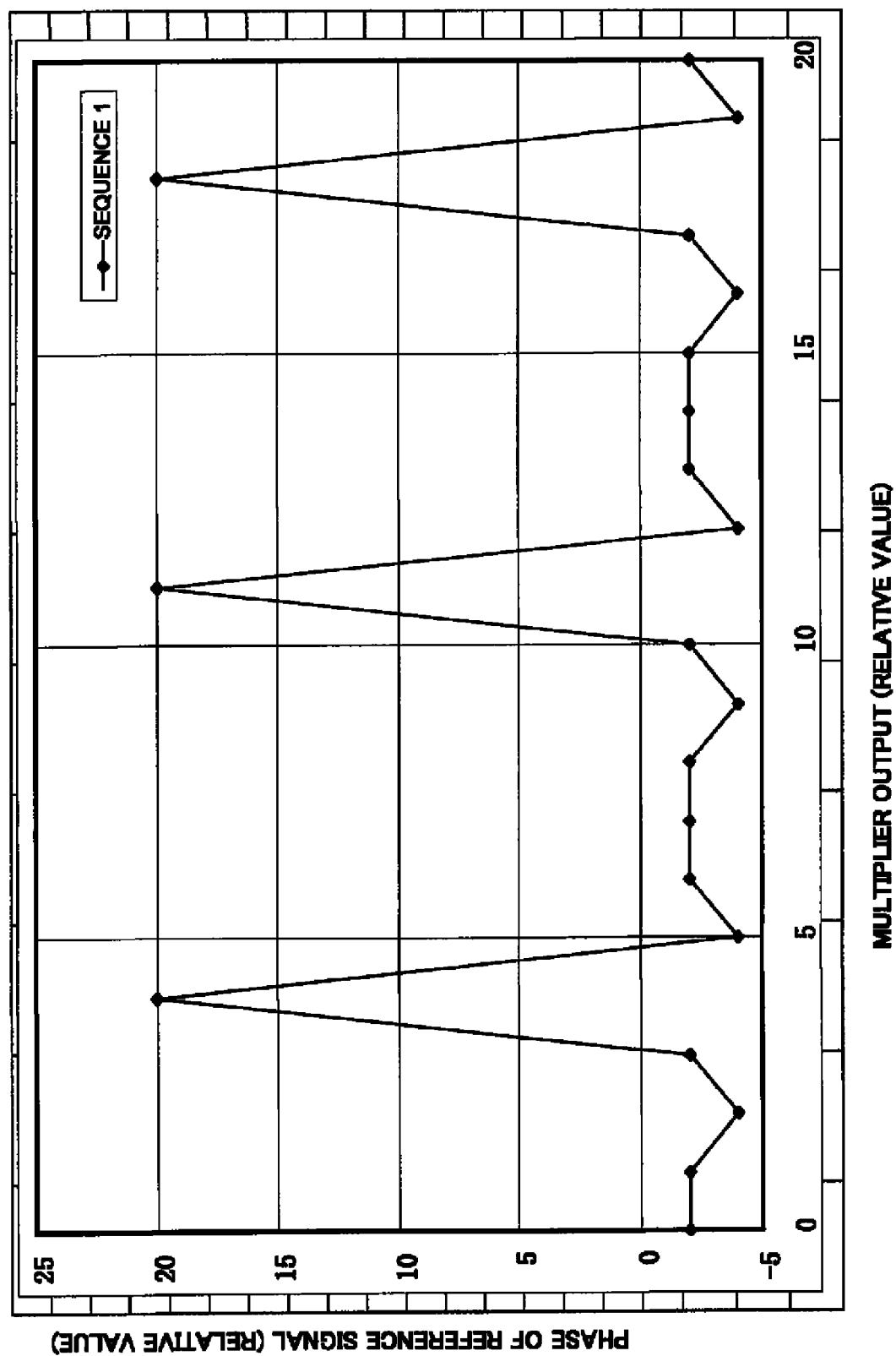
FIG. 6 is a view illustrating the relationship between a voltage output from the multiplier and the phase of a reference signal.

FIG. 6 is a view illustrating a relationship between the voltage of a multiplier output and the phase of a reference signal, and illustrates the relationship between the sum values (the voltages of the multiplier outputs) and the phases (the phases of the reference signal) shown in FIG. 5 in the form of a graph. FIG. 6 shows that only the peak values of the multiplier output which appear periodically have an extremely great value. These peak values increase in proportion to the length of the PN pattern. On the other hand, when the phase of the reference signal is other than the phases at which the peak values can be obtained, because many bits cancel each other at the time of multiplication by the multiplier, the multiplier output does not increase even when the length of the PN pattern increases. Consequently, the longer the PN pattern, the greater the ratio of the peak values to other output values. This effect is completely the same as the nature in pulse compression.

As can be known from the above, according to the present embodiment, by adjusting the phase of the reference signal so as to correspond to the delay time to the target, it is possible to selectively detect a reflection wave power and Doppler information concerning only the target depth. Also, such selectivity becomes sharper with increasing length of the pseudo random pattern. Further, as the pattern length increases, this selectivity approaches characteristics similar to the range gate of the pulse wave Doppler (PW Doppler). In other words, it is possible to obtain the merits of the pulse waves, while retaining the advantages of the continuous waves.

Figure 7:
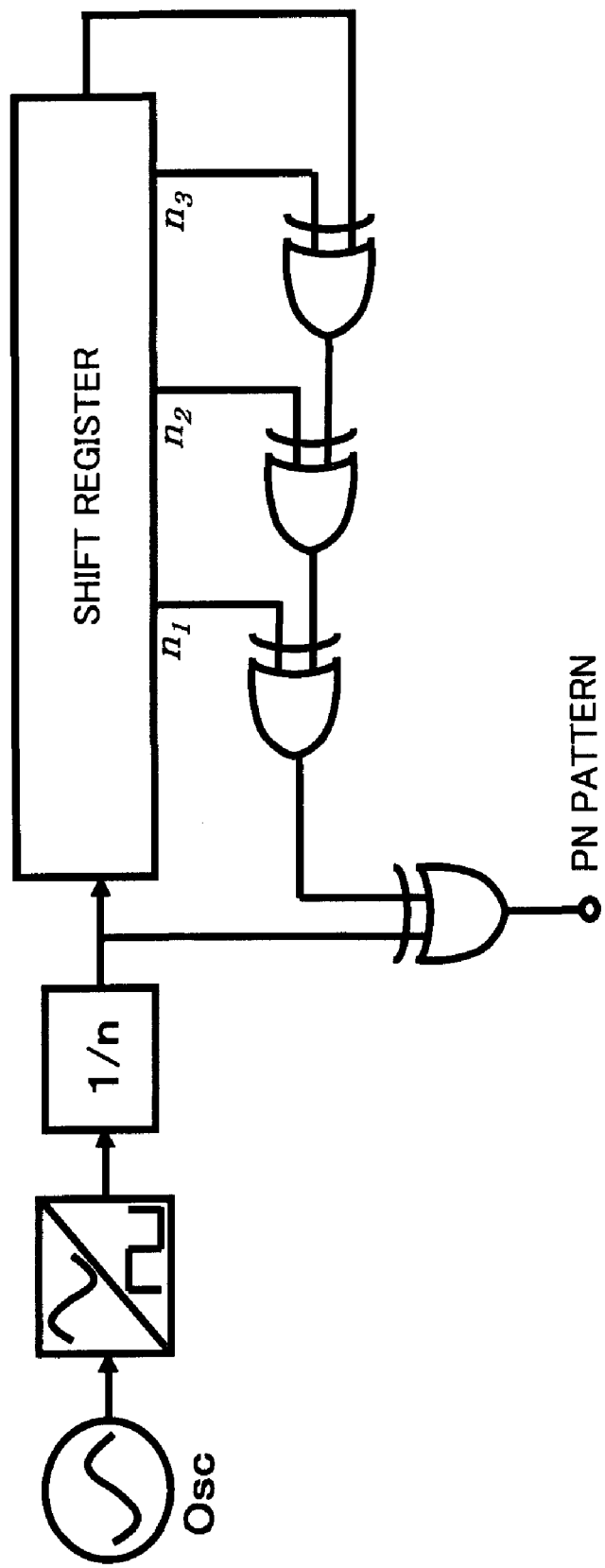
FIG. 7 is a view illustrating a specific example of a pattern generator.

FIG. 7 illustrates a specific example of the pattern generator (designated by reference numeral 24 in FIG. 1). In the example circuit structure illustrated in FIG. 7, a carrier wave (RF signal) output from a crystal oscillator (OSC) is transformed into a rectangular signal and is then n-frequency divided, and the resulting signal (data) is input to the shift register. Further, outputs of $n_1$ to $n_3$ extracted from the intermediate stages of the shift register and an output from the last stage of the shift register are utilized to obtain an exclusive OR, so that a PN pattern can be obtained. When the shift register has n stages, the length of a PN pattern is $(2^n-1)$ bits. For example, when n=10, a PN pattern of 1023 bits can be configured in a simple manner. In this case, while the multiplier output obtained when the phases of the reception signal and the reference signal are completely identical with each other is 1023 times that for 1 bit, the outputs at other portions are at most several times that for 1 bit. It is therefore possible to significantly increase the selectivity. The circuit in FIG. 7, which can be configured by a digital circuit, is also advantageous in that IC can be achieved easily.

Figure 8:
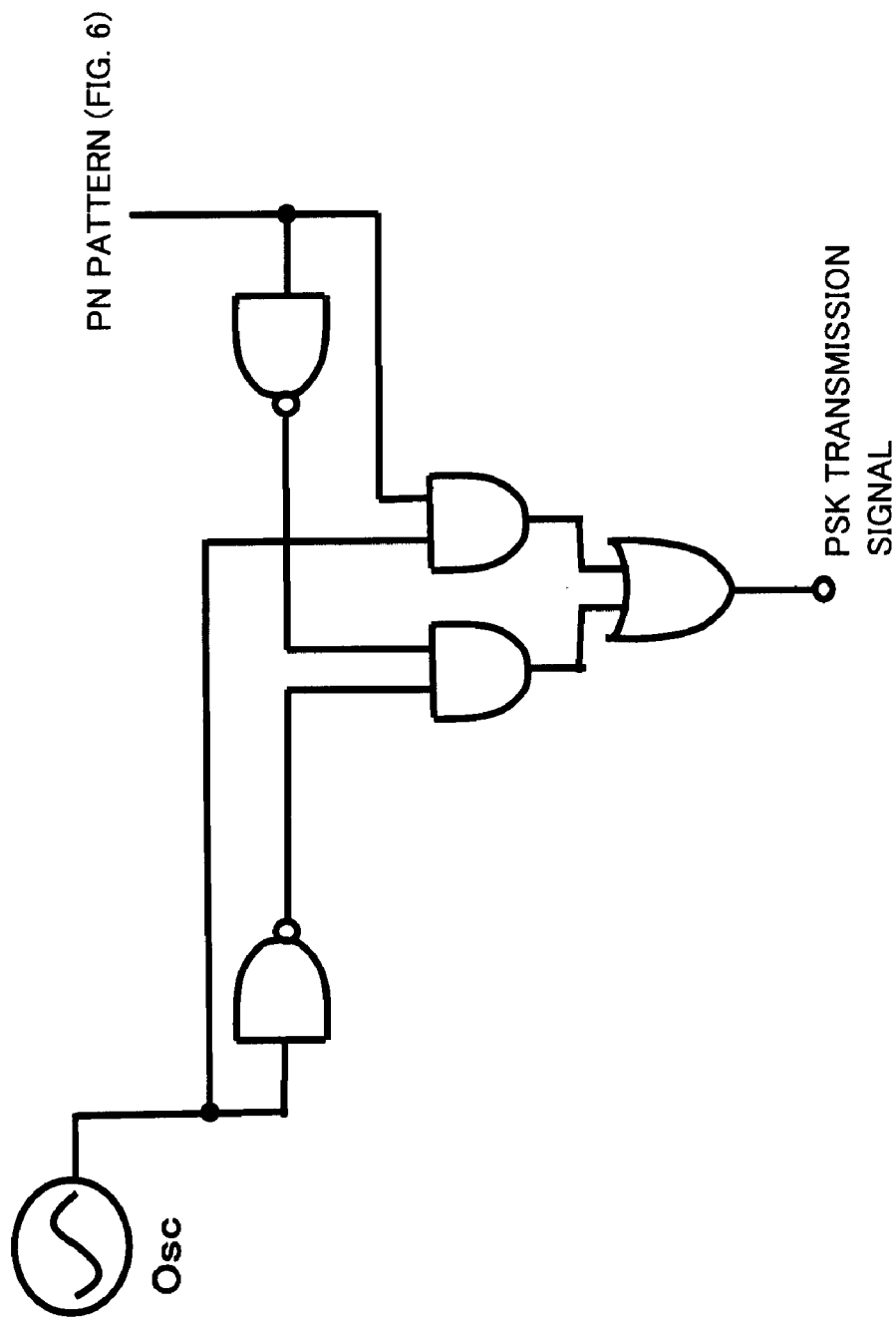
FIG. 8 is a view illustrating a specific example of a PSK modulator.

FIG. 8 illustrates a specific example of the PSK modulator (designated by reference numeral 20 in FIG. 1). The circuit shown in FIG. 8 selects either one of two types of carrier waves, which are a carrier wave (RF signal) output from the crystal oscillator (OSC) and an inverted carrier wave having an inverted phase of the carrier wave, in accordance with the polarity of the PN pattern. The carrier wave which is selected in accordance with the PN pattern is added (connected) by the OR circuit and is output as a PSK transmission signal. In this manner, the transmission signal having a waveform shown in FIG. 2(C), for example, is output. While FIG. 8 illustrates an example structure employing a digital circuit, there may be used a method in which a double balanced mixer (DBM) is used as a means of PSK modulation. Here, the circuit in FIG. 8, which can be configured by a digital circuit, is also advantageous in that IC can be achieved easily.

Figure 9:
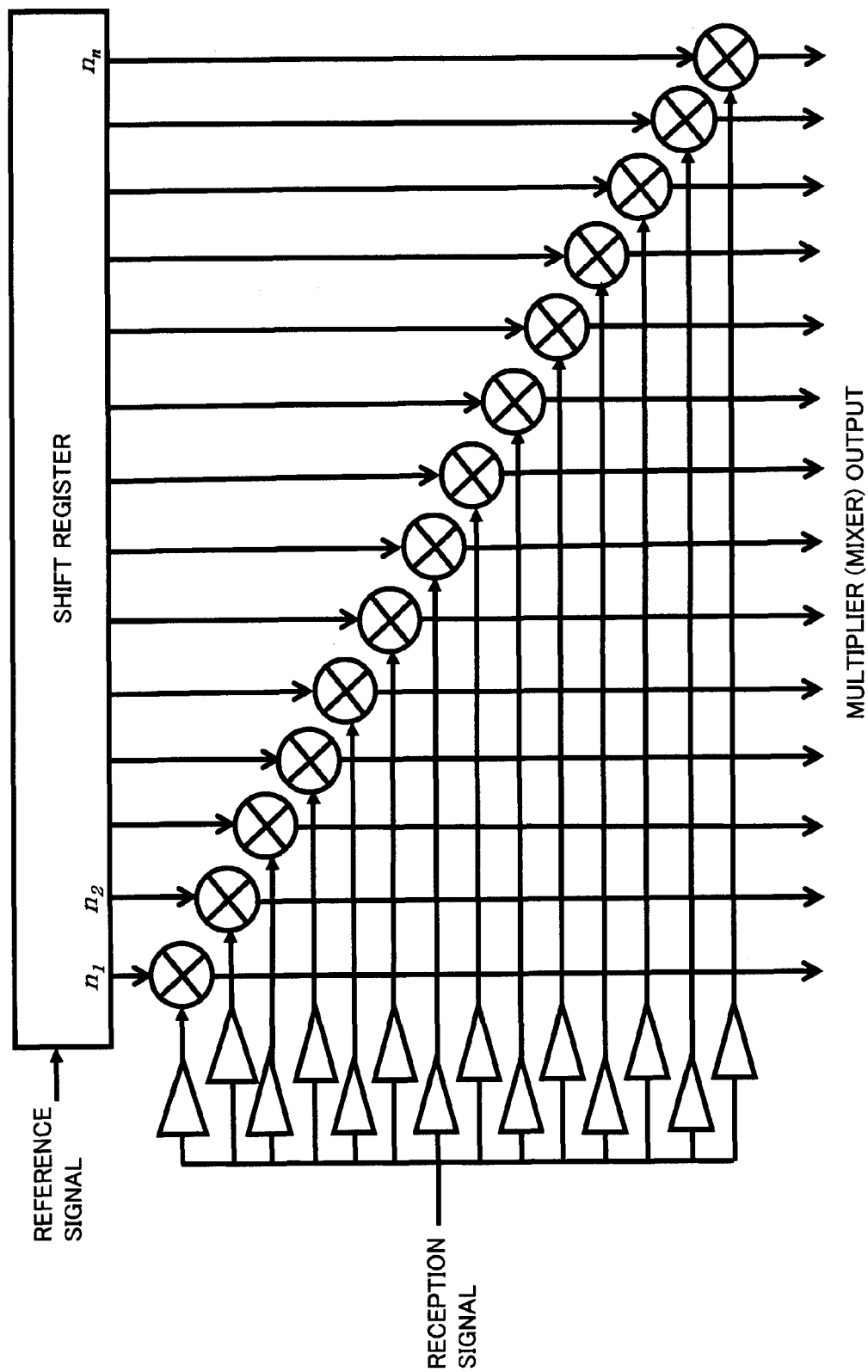
FIG. 9 is a view for explaining modification examples of a delay circuit and a receiving mixer.

FIG. 9 is a view for explaining a modification example of the delay circuit (designated by reference numerals 26I and 26Q in FIG. 1) and the receiving mixer (designated by reference numeral 30 in FIG. 1). In the circuit illustrated in FIG. 9, the reference signal is delayed by an n-stage shift register, and a plurality of delayed reference signals with different delay times with respect to each other are simultaneously output from the respective taps $n_1$ to $n_n$ of the shift register. Then, in each of n mixers corresponding to the respective taps $n_1$ to $n_n$ of the shift register, multiplication between the reception signal and each delayed reference signal is performed, so that a plurality of multiplication results corresponding to the plurality of delayed reference signals are output simultaneously (in parallel). By previously associating a plurality of target positions arranged in the depth direction within a living organism with the respective taps $n_1$ to $n_n$ of the shift register, Doppler information from a plurality of target positions can be acquired simultaneously. For example, it is possible to employ a configuration such that tissue information from all the positions on the ultrasound beam can be detected simultaneously.

While digital modulation by mean of 2-phase PSK using binary phase code, 0–π has been described in FIG. 2 and FIG. 4, in the present embodiment, it is also possible to utilize PSK with multiple phases, such as 4-phase, 8-phase, 16-phase, and so on.

Figure 10:
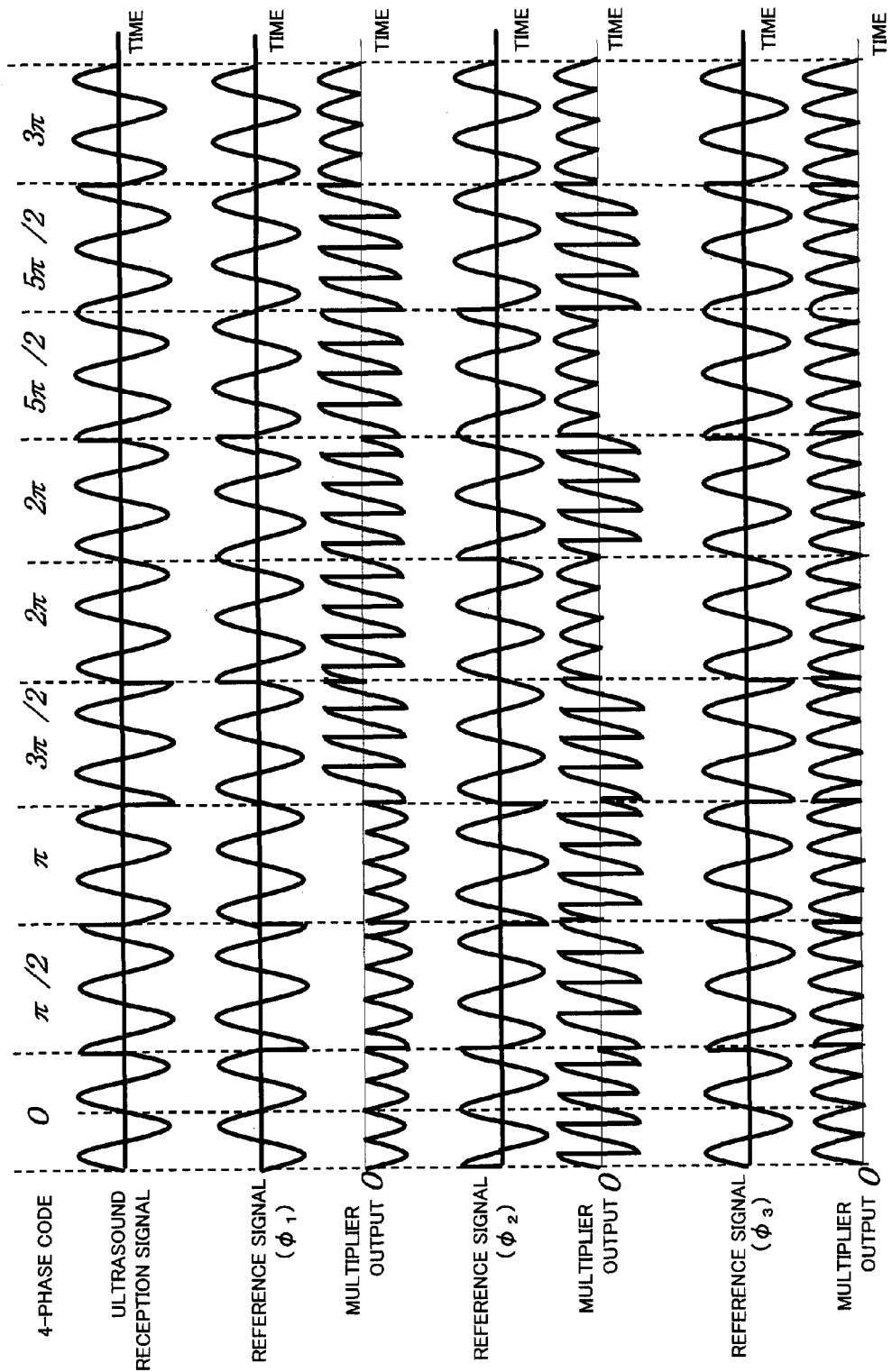
FIG. 10 is a view for explaining digital modulation by means of 4-phase PSK.

FIG. 10 is a view for explaining digital modulation by means of 4-phase PSK. FIG. 10 illustrates an example in which a 4-phase code, 0, $\pi/2$, $\pi$, $3\pi/2$, is utilized. The 4-phase code is a periodical signal sequence output from the pattern generator (designated by reference numeral 24 in FIG. 1). The PSK modulator (designated by reference numeral 20 in FIG. 1) performs modulation processing by means of applying to an RF signal phase shift keying (PSK) based on the 4-phase code. Consequently, a transmission signal having the same waveform as that of the ultrasound reception signal shown in FIG. 10 is formed. FIG. 10 illustrates results of multiplication (multiplier outputs) between the reference signal obtained by delaying the transmission signal and the reception signal while varying the phase of the reference signal from $\phi_1$ to $\phi_3$.

In the case of $\phi_3$, among the phases shown in FIG. 10, a result obtained when the delay time; i.e., the phase, is adjusted to the depth of a target is shown. It can be seen that, in this case, the reception signal and the reference signal correspond to each other at any time range. The multiplier output is obtained in such a manner that the reception signal is switched in accordance with the polarity of the reference signal, and the frequency spectrum thereof includes a direct current component and a harmonic component which is twice the carrier wave (RF signal), as with the case of 2-phase PSK illustrated in FIG. 3. These spectra are subjected to Doppler shift, and a Doppler signal appears generally with small power, as attached to the direct current component.

When the phase of the reference signal is $\phi_1$ and $\phi_2$, among the phases illustrated in FIG. 10, the phases do not correspond to the delay time. In this case, when the phase difference between the reception signal and the reference signal is $\pi/2$, the direct current component of the multiplier output is "0." When the phase difference between the reception signal and the reference signal is $\pi$, the direct current component of the multiplier output is "−1." Further, when the phase difference between the reception signal and the reference signal is 0 or $2\pi$, the direct current component of the multiplier output is "+1." Accordingly, the time-averaged multiplier output is −2 in the case of $\phi=\phi_1$ and is +3 in the case of $\phi=\phi_2$. Meanwhile, in the case of $\phi=\phi_3$, the time-averaged multiplier output is "+9," which is obviously a greater correlation value compared to the cases of $\phi=\phi_1$ and $\phi=\phi_2$.

Figure 11:
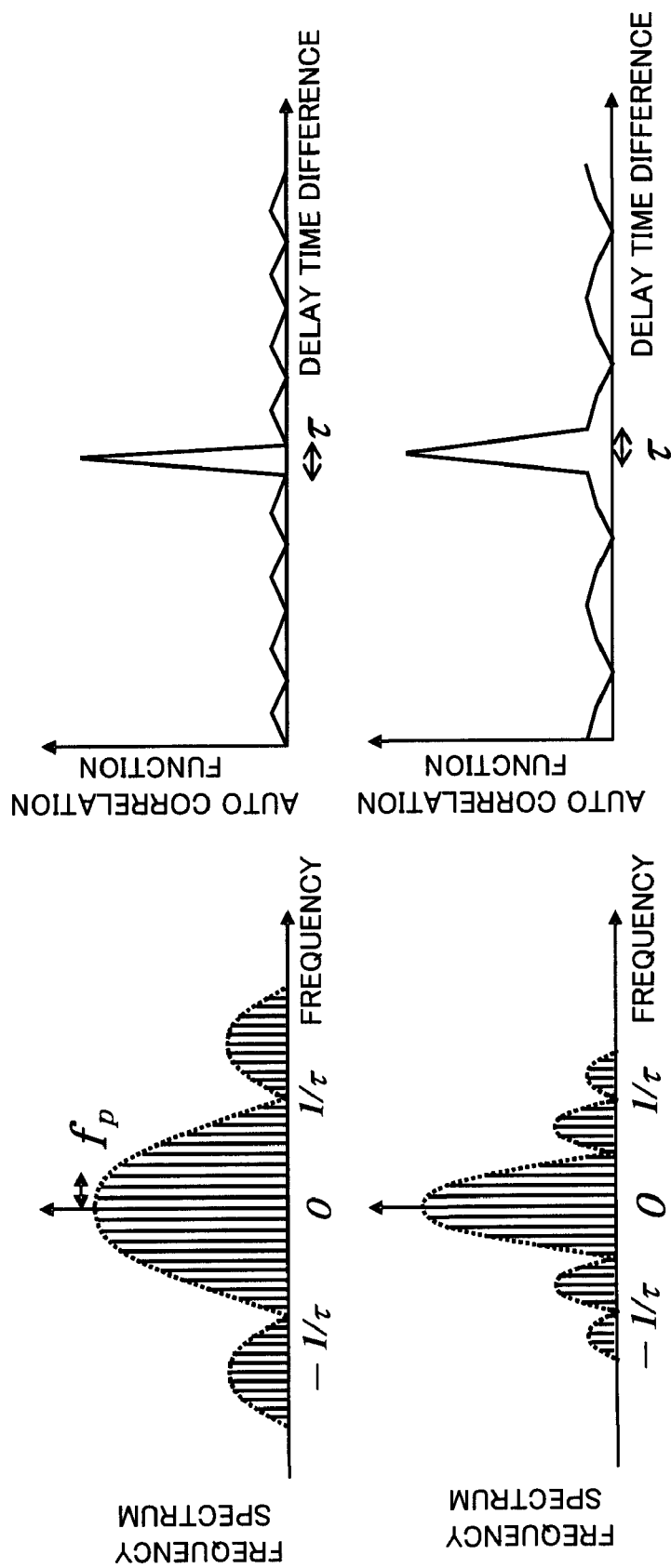
FIG. 11 is a view for explaining comparison between 2-phase (binary phase) PSK and 4-phase PSK.

FIG. 11 is a view for explaining comparison between 2-phase PSK and 4-phase PSK. In FIG. 11, the frequency spectrum and the autocorrelation function indicated in the upper section correspond to PSK with a binary phase code, 0–$\pi$, and the frequency spectrum and the autocorrelation function indicated in the lower section correspond to PSK with a 4-phase code. The 4-phase code sequence concerning the 4-phase PSK indicated in the lower section of FIG. 11 is "0, $\pi/2$, $\pi$, $3\pi/2$, $2\pi$, $2\pi$, $5\pi/2$, $5\pi/2$, $3\pi$, $3\pi$, $3\pi$, $3\pi$, $3\pi$."

Comparing the examples in the upper and lower sections in FIG. 11, the width of the peak of the autocorrelation function is slightly larger in the 4-phase PSK, whereas the bandwidth of frequency spectrum of 4-phase PSK is about half the width of that of 2-phase PSK. It is therefore understood that, with the use of 4-phase PSK, position selectivity which is substantially equal to that of the 2-phase PSK with 0–$\pi$ can be obtained even when the frequency bandwidth of an ultrasound signal is approximately halved.

The above characteristics of the 4-phase PSK can be assumed from the following grounds. First, with regard to the frequency band, in the 2-phase (binary) PSK, for every 1 bit, the phase of a carrier wave is inverted by 180° at a frequency of 1/2, and therefore the frequency band is wide. In the sequence of 4-phase PSK, on the other hand, for each bit, the phase advances only by $\pi/2$ or does not advance at all, as can be known from the above-described example sequence. Accordingly, because no abrupt phase rotation is generated in 4-phase PSK, the frequency band is narrow. In other words, in the 4-phase PSK, the occupied band is reduced to approximately one-half at the expense of a slight drop in sharpness of the autocorrelation function.

Further, it is also possible to consider that, in an ultrasound CW Doppler measuring method by means of PSK, in place of the 2-phase PSK which is adopted for pulse compression in a radar or an ultrasound diagnostic apparatus, the 4-phase PSK in which no significant phase variations occur can be sufficiently employed. Here, the number of phases is not limited to 4, and may be 8, 16, and so on.

Also, in FIG. 11, in the frequency spectrum of the 4-phase PSK (indicated in the lower section), two maximum values are generated within the band of a reciprocal $1/\tau$ of a time interval $\tau$ for 1 bit. This is because, in 4-phase, the frequency of successive occurrence of two identical phases is high. The advantages described above are completely the same as those in pulse compression.

Figure 12:
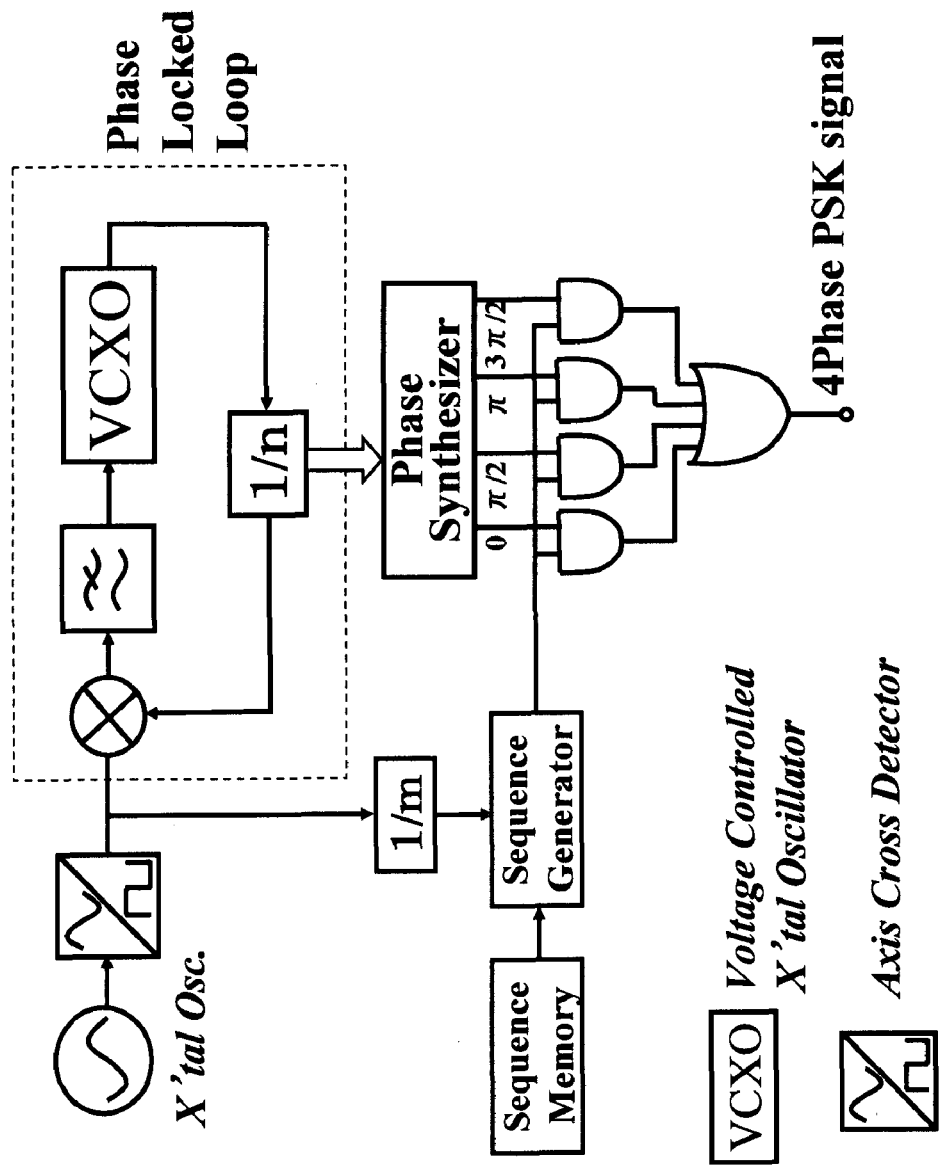
FIG. 12 is a view illustrating a specific example of a PSK modulator in the case of 4-phase PSK.

FIG. 12 illustrates a specific example of a PSK modulator employed in the case of 4-phase PSK. In the circuit illustrated in FIG. 12, an output from a crystal oscillator (X'tal Osc.), after being transformed by a transformer (Axis Cross Detector) to a logic level, is input to a phase locked loop (PLL). The PLL generates four signals which are in synchronization with the frequencies of the crystal oscillator. The four signals are output from a phase synthesizer as carrier waves maintaining the phase relationship of 0, $\pi/2$, $\pi$, and $3\pi/2$.

A sequence generator sets a 4-phase sequence based on data obtained from a sequence memory and, in accordance with the 4-phase sequence, selects one of four AND circuits. As a result, the 4-phase carrier waves output from the phase synthesizer are selectively utilized in accordance with a digital signal which sets the 4-phase sequence generated by the sequence generator, and are finally added (connected) by an OR circuit and output as a 4-phase PSK transmission signal. Thus, a transmission signal having the same waveform as that of the ultrasonic reception signal illustrated in FIG. 10, for example, is output.

As a matter of course, while a means for generating a 4-phase PSK transmission signal by a digital circuit is illustrated in FIG. 12, a method in which a plurality of double balanced mixers (DBM) are used, for example, can be utilized as a means of 4-phase PSK modulation. Here, the circuit illustrated in FIG. 12, which can be configured by a digital circuit, is suitable for IC.

Here, as pattern examples which sharpen the correlation of a 4-phase code sequence, "0, $\pi/2$, $\pi$, $3\pi/2$, $2\pi$, $2\pi$, $5\pi/2$, $5\pi/2$, $3\pi$, $3\pi$, $3\pi$, $3\pi$, $3\pi$," "0, 0, 0, 0, 0, $\pi/2$, $\pi/2$, $\pi$, $\pi$, $3\pi/2$, $2\pi$, $5\pi/2$, $3\pi$," and so on can be utilized in the case of 13 bits, and "0, 0, 0, 0, 0, $\pi/2$, $\pi/2$, $\pi/2$, $\pi$, $\pi$, $3\pi/2$, $3\pi/3$, $2\pi$, $5\pi/2$, $5\pi/2$, $3\pi$, $7\pi/2$, $4\pi$, $9\pi/2$" can be utilized in the case of 19 bits.

While a preferred embodiment of the present invention and some modification examples have been described, they are merely illustrative examples in various terms, and do not therefore limit the scope of the present invention.

For example, while, in the embodiment described above, phase shift keying (PSK) is utilized for digitally modulating a continuous wave, frequency shift keying (FSK), amplitude shift keying (ASK), or the like, which to those with ordinary skill in the art are obviously available as digital modulation methods, may be utilized in place of PSK. Here, it is also possible to store data of a digitally modulated continuous wave in a memory and so on and generate the continuous wave based on the data read from the memory.

What is claimed is:

1. An ultrasound diagnostic apparatus comprising:
a transmission signal processing unit that outputs a transmission signal which is a continuous wave having been digitally modulated based on a periodical signal sequence;
a transmitting/receiving unit that transmits a transmission wave corresponding to the transmission signal to a living organism and receives a reception wave associated with the transmission wave from the living organism, to thereby obtain a reception signal;
a reception signal processing unit that applies demodulation processing to the reception signal by using a reference signal formed based on the transmission signal, to thereby obtain a demodulated signal; and
a Doppler information extraction unit that extracts Doppler information from the demodulated signal,
wherein
Doppler information from a target position within the living organism is selectively extracted.

2. The ultrasound diagnostic apparatus according to claim 1, wherein
the transmission signal processing unit outputs a transmission signal which is a continuous wave formed by means of phase shift keying.

3. The ultrasound diagnostic apparatus according to claim 2, wherein
the transmission signal processing unit outputs a transmission signal which is a continuous wave formed by varying a phase of a carrier wave signal by means of phase shift keying based on a periodical signal sequence.

4. The ultrasound diagnostic apparatus according to claim 1, wherein
the reception signal processing unit applies demodulation processing to the reception signal by using the reference signal having a waveform which is identical with that of the transmission signal.

5. The ultrasound diagnostic apparatus according to claim 1, wherein
the transmission signal processing unit outputs a transmission signal which is a continuous wave formed by varying a phase of a carrier wave signal by means of phase shift keying based on a periodical signal sequence, and
the reception signal processing unit applies demodulation processing to the reception signal by using the reference signal having a waveform which is identical with that of the transmission signal.

6. The ultrasound diagnostic apparatus according to claim 5, wherein
Doppler information from the target position is selectively extracted by applying the demodulation processing with a correlation between a periodical signal sequence of the reception signal obtained from the target position within the living organism and a periodical signal sequence of the reference signal being adjusted.

7. The ultrasound diagnostic apparatus according to claim 6, wherein
by delaying the reference signal by a delay amount in accordance with a depth of the target position, a signal sequence pattern of the reception signal obtained from the target position and a signal sequence pattern of the reference signal are matched to each other.

8. The ultrasound diagnostic apparatus according to claim 1, wherein
Doppler information from the target position is selectively extracted by applying the demodulation processing with a correlation between a periodical signal sequence of a reception signal obtained from the target position within the living organism and a periodical signal sequence of the reference signal being adjusted.

9. The ultrasound diagnostic apparatus according to claim 8, wherein
the correlation is adjusted by applying delay processing in accordance with a depth of the target position within the living organism to thereby adjust a delay relationship between the reception signal and the reference signal.

10. The ultrasound diagnostic apparatus according to claim 9, wherein
with the delay processing, a correlation between the periodical signal sequence of the reception signal and the periodical signal sequence of the reference signal is enhanced.

11. The ultrasound diagnostic apparatus according to claim 10, wherein
by delaying the reference signal by a delay amount in accordance with a depth of the target position, a signal sequence pattern of the reception signal obtained from the target position and a signal sequence pattern of the reference signal are matched to each other.

12. The ultrasound diagnostic apparatus according to claim 1, wherein
the Doppler information extraction unit extracts, as the Doppler information, a Doppler signal component corresponding to a direct current signal component contained in the demodulated signal.

13. The ultrasound diagnostic apparatus according to claim 1, wherein
the transmission signal processing unit outputs a transmission signal which is a continuous wave formed by varying a phase of a carrier wave signal by means of phase shift keying based on a periodical signal sequence,
the reception signal processing unit applies demodulation processing to the reception signal by using the reference signal having a waveform which is identical with that of the transmission signal, and
the Doppler information extraction unit extracts, as the Doppler information, a Doppler signal component corresponding to a direct current signal component contained in the demodulated signal.

14. The ultrasound diagnostic apparatus according to claim 13, wherein
the Doppler information from the target position is selectively extracted by applying the demodulation processing with a correlation between a periodical signal sequence of the reception signal obtained from the target position within the living organism and a periodical signal sequence of the reference signal being adjusted.

15. The ultrasound diagnostic apparatus according to claim 1, further comprising:
a delay processing unit that delays the reference signal based on a plurality of different delay amounts, to thereby form a plurality of delayed reference signals corresponding to a plurality of target positions,
wherein
the reception signal processing unit applies demodulation processing to the reception signal by using the plurality of reference signals, to thereby form a plurality of demodulated signals corresponding to the plurality of target positions, and
the Doppler information extraction unit extracts, based on the plurality of demodulated signals, Doppler information from the plurality of target positions arranged in a depth direction within the living organism.

* * * * *